United States Patent [19]

Au et al.

[11] Patent Number: 5,362,480
[45] Date of Patent: Nov. 8, 1994

[54] ORAL HYGIENE COMPOSITIONS CONTAINING AMINO SUGARS AS ANTIPLAQUE AGENTS

[75] Inventors: Van Au, Peekskill, N.Y.; Robert G. Carson, Rahway, N.J.; Bijan Harirchian, South Orange, N.J.; Kurt M. Schilling, Verona, N.J.

[73] Assignee: Lever Brothers Company, Division of Conopco, Inc., New York, N.Y.

[21] Appl. No.: 981,973

[22] Filed: Nov. 25, 1992

Related U.S. Application Data

[63] Continuation-in-part of Ser. No. 816,407, Dec. 31, 1991, abandoned.

[51] Int. Cl.$^5$ .......................... A61K 7/16; A61K 7/18; A61K 7/22
[52] U.S. Cl. ........................ 424/54; 424/49; 424/52
[58] Field of Search ................ 424/49, 52, 54, 48

[56] References Cited

U.S. PATENT DOCUMENTS

| | | | |
|---|---|---|---|
| 4,218,487 | 8/1980 | Jaeggi | 426/533 |
| 4,329,333 | 5/1982 | Barr | 424/54 |
| 4,446,125 | 5/1984 | Mookherjee et al. | 424/49 |
| 4,590,067 | 5/1986 | Meisner | 514/902 |
| 4,638,816 | 1/1987 | Cox et al. | 131/276 |
| 4,647,453 | 3/1987 | Meisner | 424/54 |
| 4,663,202 | 5/1987 | Causton | 424/49 |
| 4,683,222 | 7/1987 | Stadler et al. | 514/42 |
| 4,710,491 | 12/1987 | Lochoff et al. | 536/22 |
| 4,737,359 | 4/1988 | Eigen et al. | 424/50 |
| 4,737,488 | 4/1988 | Lockhoff et al. | 514/42 |
| 4,772,591 | 9/1988 | Meisner | 514/474 |
| 4,855,128 | 8/1989 | Lynch et al. | 424/49 |
| 4,877,603 | 10/1989 | Degenhardt et al. | 424/52 |
| 4,913,894 | 4/1990 | Curtis et al. | 514/817 |
| 4,992,420 | 2/1991 | Neeser | 424/49 |
| 4,994,441 | 2/1992 | Neeser | 424/49 |
| 5,000,973 | 3/1991 | Scaglione et al. | 426/549 |
| 5,002,759 | 3/1991 | Gaffar et al. | 424/49 |
| 5,015,485 | 5/1991 | Scaglione et al. | 426/94 |
| 5,047,231 | 9/1991 | Spanier et al. | 426/646 |
| 5,071,977 | 12/1991 | Cassels et al. | 536/123 |
| 5,095,106 | 3/1992 | Gaffar et al. | 536/123 |
| 5,202,113 | 4/1993 | London | 424/49 |
| 5,217,715 | 6/1993 | Krivan et al. | 424/92 |

FOREIGN PATENT DOCUMENTS

| | | |
|---|---|---|
| 0057323 | 8/1982 | European Pat. Off. . |
| 0178602 | 4/1986 | European Pat. Off. . |
| 0285178 | 10/1988 | European Pat. Off. . |
| 0413675A2 | 2/1991 | European Pat. Off. . |
| 3112904 | 5/1991 | Japan . |
| 3112905 | 5/1991 | Japan . |
| 2224204 | 5/1990 | United Kingdom . |
| WO91/02530 | 3/1991 | WIPO . |
| WO92/05764 | 4/1992 | WIPO . |

OTHER PUBLICATIONS

Streitwieser, A. et al., "Introduction to Organic Chemistry" Third Edition (1985), pp. 894, 899 and 915.
European Search Report published Apr. 19, 1993 in a counterpart European Patent Application 92203981.3.
American Chemical Society, "Chemical Abstracts", vol. 93, No. 20, Nov. 10–24, 1980, Abstract No. 191921d.
Chemical Abstracts 115:57205t (1991).
Chemical Abstracts 93:191921d (1980).
Chemical Abstracts 110:13402x (1989).

(List continued on next page.)

Primary Examiner—Ronald W. Griffin
Attorney, Agent, or Firm—Rimma Mitelman

[57] ABSTRACT

Oral hygiene antiplaque compositions which include as an active ingredient an amino sugar containing a sugar moiety recognized by lectins on oral bacteria (e.g., $\beta$-D-galactose, $\beta$-D-N-acetyl galactosamine, L-rhamnose and $\beta$-D-fucose) and in which nitrogen is linked to carbon number 1. The amino sugars singly or in combination with each other provide enhanced inhibition of bacterial aggregation, surfactancy, and antimicrobial activity.

17 Claims, No Drawings

OTHER PUBLICATIONS

Stromberg, Nicklas et al. "Characterization of the Binding of *Actinomyces naeslundii* (ATCC 12104) and *Actinomyces viscosus* (ATCC 19246) to Glycosphingolipids, Using a Solid–phase Overlay Approach", The Journal of Biological Chemistry, vol. 265, No. 19 (Jul. 5, 1990), pp. 11251–11258.

Stromberg, Nicklas et al., Abstracts of International Association for Dental Research Scandinavian Division, Helsinki, Abstract No. 10, Aug. 22–24, 1991.

Stromberg, Nicklas et al., Abstracts of International Association for Dental Research Scandinavian Division, Helsinki, Abstract No. 12, Aug. 22–24, 1991.

McIntire, Floyd C. et al. "Structural Preferences of β–Galactoside–Reactive Lectina on *Actinomyces viscosus* T14V and *Actinomyces naeslundii* WVU45", Infection and Immunity, vol. 41, No. 2, (Aug. 1983), pp. 848–850.

Rosenberg, Eugene et al. "Inhibition of Bacterial Adherence to Hydrocarbons and Epithelial Cells by Emulsion", Infection and Immunity, vol. 39, No. 3, (Mar. 1983), pp. 1024–1028.

Gibbons, R. J. "Bacterial Adhesion to Oral Tissues: A Model for Infectious Diseases", Journal of Dental Research, vol. 68 No. 5, (May 1989), pp. 750–760.

Kolenbrander, Paul E. "Surface Recognition Among Oral Bacteria: Multigeneric Coaggregations and Their Mediators", Critical Reviews in Microbiology, vol. 17, Issue 2 (1989), pp. 137–159.

Dibdin, G. H. et al. "Physical and Biochemical Studies of Streptococcus mutane Sediments Suggest New Factors Linking the Cariogencity of Plaque with its Extracellular Polysaccharide Content", J. Dent. Res., vol. 67, No. 6, (Jun. 1988), pp. 890–895.

Latge, P. et al. "Synthesis of Long Chain N-Alkyllactylamines from Unprotected Lactose: A New Seriew of Non–Ionic Surfactants", Dispersion Science and Technology, 12 (3&4)(1991), pp. 227–237.

Abstract of European Patent Application 184 121.

Tatevossian, A. "Diffusion of Radiotracers in Human Dental Plaque", Caries Res., 13:154–162, (1979).

ORAL HYGIENE COMPOSITIONS CONTAINING AMINO SUGARS AS ANTIPLAQUE AGENTS

This is a continuation-in-part of copending application Ser. No. 07/816,407, filed Dec. 31, 1991, now abandoned.

FIELD OF THE INVENTION

The invention relates to oral hygiene compositions which inhibit formation and/or growth of bacteria responsible for dental plaque.

BACKGROUND OF THE INVENTION

It is generally recognized that the development of dental plaque begins with the adhesion of bacteria to the teeth. Bacterial adhesion to tooth surfaces usually involves stereospecific interactions between cell surface binding proteins, referred to as adhesins, and cognate structures which form binding sites either in salivary pellicle, or on the surfaces of other bacteria resident in plaque, or in the extracellular plaque matrix (Gibbons, R. J.; J Dent Res 68,750–760).

Many of the oral bacterial adhesins described in the art exhibit carbohydrate-specific binding and are often found on filamentous extensions (i.e., pili or fimbriae) which protrude from cell surfaces. These carbohydrate recognition structures, which are also referred to as lectins, mediate binding to host-derived or microbial-derived saccharide-containing structures on the teeth. Several different bacterial lectins have been described in the literature. Fucose-specific lectins have been described for several oral bacterial species, including those belonging to the genera Actinomyces, Capnocytophaga, and Streptococcus. Rhamnose-specific lectins have been isolated from oral species including Capnocytophaga sp.

By far, the lectins most commonly expressed by plaque bacteria are β-galactoside-specific or "lactose sensitive" adhesins. The genera of bacteria which produce β-galactoside-specific adhesins cover a diverse taxonomic range, including Actinomyces, Streptococcus, Porphyromonas, Fusobacterium, Haemophilus, Capnocytophaga, Veillonella, Prevotella, Staphylococcus, and Neisseria; these represent both primary and secondary colonizers of the teeth (Kollenbrander, P. E.; Crit Rev Microbiol 17:137–159). Kollenbrander notes that bacterial coaggregation plays an active role in formation of dental plaque and adherence of bacteria to epithelial cells in the oral econiche.

Most attempts to control plaque through anti-adhesion mechanisms have involved non-stereospecific inhibition of bacterial attachment to the teeth, usually with compositions containing surface-active polymers. For instance, G. B. Pat. No. 2,224,204A and U.S. Pat. No. 4,877,603 disclose oral compositions which include phosphonate-containing polymers that inhibit bacterial attachment to hydroxyapatite surfaces. Similarly, U.S. Pat. No. 4,663,202 discloses a method for treating surfaces with combinations of polymers which form barriers that retard bacterial adsorption.

With respect to blocking stereospecific interactions which mediate oral bacterial adherence, the use of mono- and oligosaccharides has been described, as inhibitors of lectin-mediated adhesion to human cells. For instance, abstract of U.S. Pat. No. 7,349,772 describes oligosaccharides isolated from *S. sanguis* which inhibit the build-up of adhesive dental plaque. Gaffar et al. (U.S. Pat. No. 5,002,759) disclose oligosaccharides containing either a galactose moiety (which may be β-galactose) and/or a fucose moiety as agents in dentifrice preparations for inhibiting adherence of *Streptococcus pyogenes* to human epithelial cells. European Patent Application 184,121 discloses the use of galactose and/or lactose as anti-caries agents in foods, drinks, and pharmaceutical preparations. Neeser (U.S. Pat. Nos. 4,992,420 and 4,994,441) describes kappa-caseinoglycopeptide compounds and desialylated derivatives thereof (the derivatives contain β-galactose groups) as inhibitors of in vitro adhesion by dental plaque bacteria to human erythrocytes.

Lynch et al. (U.S. Pat. No. 4,855,128) disclose polysaccharides such as xanthan gum, gum tragacanth, guar gum, gum karaya, chondroitin sulfate, polygalacturonic acid, (pectin) sodium alginate and carrageenans of the kappa/lambda configuration as plaque-inhibitory agents which inhibit bacterial coaggregation; carrageenans of kappa/lambda configuration and chondroitin sulfate contain β-galactose.

Stromberg et al. (J. Biol. Chem. 265,11251–11258) disclose that N-acetyl-galactosamine-β1,3-galactose-O-ethyl is an inhibitor of binding by *Actinomyces viscosus* and *Actinomyces naeslundii* to human erythrocytes. McIntire et al. (Infection and Immunity, vol. 41, No. 2, 848–850) have described O-glycosides of galactose-β1,3-N-acetyl-galactosamine, including phenyl, phenylethyl, and nitrophenyl derivatives, which inhibit coaggregation between Actinomyces sp., and *Streptococuus sanguis;* McIntire et al. note that the addition of aglycones increased the inhibitory activity significantly but not greatly.

Stromberg et al. ("Synthetic Receptoranalogues Prevent Plaque Formation in Man", Abstracts of International Association for Dental Research Scandinavian Division, Helsinki, Aug. 22–24, 1991) disclose a study demonstrating the plaque inhibitory activity of GalNAcβ-3Galα1-O-ethyl, which blocked adherence of Actinomyces strains 12104 and LY7. Clinical plaque strains were evaluated in a mouth rinse experiment including five human individuals. The study is said to demonstrate that receptor analogues such as GalNAcβ-3Galα1-O-ethyl, may prove useful in future antiplaque therapy. O-glycosides described by Stromberg and McIntire are structurally different from glycosylamines included in applicants' invention. In the latter compounds, nitrogen is connected to carbon number 1, whereas in the O-glycosides described by Stromberg and McIntire nitrogen is connected to carbon number 2. Further, O-glycosides described by the Stromberg and McIntire references are expensive molecules and their synthesis is complicated; hence, their practical utility is limited to the study of the stereospecificity of bacterial binding. By contrast, glycosylamines included in the present invention are relatively inexpensive and synthetically versatile.

As to non-dental art, abstracts of Japanese Patent Applications 03112905 and 03112904 disclose the use, as antibacterials for preserving food and cosmetics, of 2-acetylamino-N-alkyl-glycosylamines and alkyl-glycosyl-amines, particularly glucosamines represented by structures 1 and 2, respectively.

STRUCTURE 1

-continued

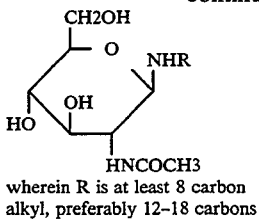

HNCOCH3
wherein R is at least 8 carbon
alkyl, preferably 12-18 carbons

STRUCTURE 2

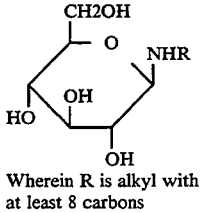

OH
Wherein R is alkyl with
at least 8 carbons

The Japanese disclosures are not aimed at delivering antiplaque or antiadhesion benefits or at affecting oral indigenous bacteria or at targeting β-galactoside specific binding proteins on oral bacteria. None of the bacteria listed in the Japanese patents are involved in dental plaque formation.

Rosenberg et al. (Infection and Immunity, March 1983, 1024–1028) disclose that emulsan, which consists of D-galactosamine (anomeric structure not reported) containing polysaccharide backbone with covalently linked fatty acid chains, prevents adherence of *A. calacoaceticus* and *S. pyogenes* to buccal epithelial cells and is highly effective in removing bound indigenous bacteria. Emulsan is a polyanionic heteropolysaccharide with a molecular weight average of $9.9 \times 10^5$ Like in the Stromberg and McIntire compounds discussed above, in the galactosamine units of emulsan nitrogen is connected carbon number 2 as opposed to the present compounds where the linkage is at carbon number 1. Eigen et al. (U.S. Pat. No. 4,737,359) disclose toothpaste or mouthwash preparations containing emulsan. Emulsan is said to reduce plaque formation by inhibiting attachment of *S. mutans*, which is said to be due to the presence of a galactosamine-specific lectin on the surface of *S. mutans*. Eigen et al. note the possibility that emulsan acts by breaking the bacterial lectin-carbohydrate interactions.

While emulsan may be an effective plaque inhibitor, emulsan must be produced by biotechnological procedures, i.e. through fermentation procedures which require extensive downstream processing and purification and which are relatively expensive. Since the production of emulsan is dependent on bacteria, emulsan cannot be easily modified (modification requires post-synthetic chemical treatment). Therefore, the use of material which can be produced and modified by synthetic procedures which are relatively less complex and less expensive than the biotechnological procedures involved in production of emulsan, would be desirable.

Accordingly, it is an object of the present invention to provide oral hygiene compositions which include specific N-containing derivatives of saccharides which include at least one β-D-galactose group, or β-D-N-acetyl galactosamine group, or β-D-fucose group, or L-rhamnose group as antiplaque agents.

It is another object of the present invention to provide oral hygiene compositions which contain effective yet commercially feasible antiplaque amino sugars.

It is another object of the invention to provide oral hygiene compositions which include antiplaque agents which can be produced and modified by synthetic procedures.

It is still another object of the invention to provide methods of inhibiting bacterial adhesion and/or bacterial growth in the oral cavity.

These and other objects of the invention will become more apparent from the detailed description and examples that follow.

SUMMARY OF THE INVENTION

The above objects are accomplished by the present invention which includes oral hygiene compositions containing:

an effective plaque-inhibiting amount of at least one compound having a formula:

$$A^1\text{-NRR}^1$$

wherein $A^1$ is a saccharide comprising at least one sugar moiety selected from the group consisting of β-D-galactose, β-D-N-acetyl galactosamine, L-rhamnose (α or β anomeric form), and β-D-fucose and wherein R and $R^1$ are the same or different and are selected from the group consisting of hydrogen, an aliphatic hydrocarbon radical, an aromatic radical, and a cycloaliphatic radical. In the amino sugars included in the inventive compositions N (Nitrogen) or substituted N is linked to the anomeric carbon at the reducing end of the saccharide $A^1$.

Preferably, to simplify synthesis and to reduce the cost of the antiplaque agents, $A^1$ is β-D-galactose or a disaccharide (i.e. lactose).

The inventive dental compositions incorporate amino sugars which singly or in combination with each other provide enhanced inhibition of bacterial aggregation, surfactancy, and antimicrobial activity. The inventive compositions inhibit adhesion and/or growth of bacteria responsible for dental plaque, thereby preventing the plaque formation, plaque-induced diseases, calculus formation, dental caries, gingivitis, and periodontal disease.

The compositions of the present invention may be in the form of toothpastes, mouthwashes, tooth powders, gels, as well as other oral delivery vehicles. The antiplaque compositions of the invention are oral non-food compositions suitable for topical application to tooth surfaces, preferably the compositions are in the form of toothpaste cream or gel or mouthwash.

The invention also includes methods of inhibiting plaque formation and growth which include applying the inventive compositions into the oral cavity.

DETAILED DESCRIPTION OF THE INVENTION

Oral hygiene compositions of the invention include as an essential antiplaque ingredient at least one amino glycoside having a formula $A^1$-NRR$^1$ wherein $A^1$ is a saccharide containing a sugar moiety selected from the group consisting of β-D-galactose, β-D-N-acetyl galactosamine, L-rhamnose, and β-D-fucose. $A^1$ is preferably β-D-galactose or lactose in order to reduce cost and simplify synthesis. In the amino sugars included in the inventive compositions, N is linked to the anomeric carbon at the reducing end of the saccharide $A^1$.

R and $R^1$ are the same or different and are selected from the group consisting of hydrogen, an aliphatic hydrocarbon radical, an aromatic radical, and a cycloaliphatic radical.

Aliphatic hydrocarbon radicals include saturated and unsaturated radicals including but not limited to methyl, ethyl, amyl, hexyl, heptyl, nonyl, decyl, undecyl, dodecyl, tridecyl, tetradecyl, pentadecyl, hexadecyl, heptadecyl, and octadecyl, and allyl, undecenyl, oleyl, linoleyl, linolenyl, propenyl, and heptenyl. The active compounds of the inventive compositions may contain straight or branched aliphatic groups. Aromatic radicals are exemplified by benzyl, aniline, or substituted benzyl or aniline groups. Suitable mixed aliphatic aromatic radicals are exemplified by benzyl, phenyl ethyl, phenoxy ethyl, and vinyl benzyl. Cycloaliphatic radicals are exemplified by but not limited to cyclopentyl and cyclohexyl.

R and $R^1$ may contain heteroatoms such as N, O, or S, present for instance as an amide, carboxy, ether, amino acids and/or saccharide moieties. Generally, R and $R^1$ contain up to 36 carbon atoms.

Preferably, to simplify synthesis R is hydrogen. On the other hand, however, a particular advantage of molecules wherein neither R nor $R^1$ are hydrogen, but are hydrocarbon radicals (for instance aliphatic radicals) is increased water solubility. Thus, increased solubility is observed when R is methyl instead of hydrogen.

In the preferred compounds, R and/or $R^1$ contain from 1 to 24 carbon atoms, preferably from 6 to 18 carbon atoms in order to attain optimum surface activity and antimicrobial activity of the amino sugars. Of course, other R and $R^1$ radicals not listed above but within the scope of the invention may be employed. Likewise, other saccharides may be employed as long as a requisite sugar moiety, i.e. β-D-galactose, or β-D-N-acetyl galactosamine or L-rhamnose or β-D-fucose is present.

It should also be noted that studies (e.g. Tatevossian, Diffusion of Radiotracers in Human Dental Plaque, Caries Research 13 (1979), 154–162) have shown that while low molecular weight carbohydrates, such as mono- and disaccharides diffuse readily through plaque, larger carbohydrate structures such as inulin and starch were restricted. Increased diffusivity in plaque is preferred in order to get penetration of the active into the plaque matrix to the specific binding sites. Consequently, the molecular weight of the amino sugars is not greater than 30,000 Daltons; preferably not greater than 20,000, most preferably the molecular weight is in the range of from 200 to 2,000 Daltons. In that respect, it is also preferred that the amino sugars are water-soluble in order to ease the formulation, particularly of toothpaste and mouthwash compositions, and to increase the diffusibility of the amino sugars into plaque matrix. The compounds of the invention are exemplified by but not limited to the following structures (A–H):

EXAMPLES OF AMINO SUGARS SUITABLE FOR THE INVENTIVE ANTIPLAQUE COMPOSITIONS:

β-Galactosylamine A

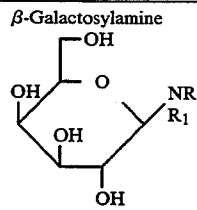

-continued
EXAMPLES OF AMINO SUGARS SUITABLE FOR THE INVENTIVE ANTIPLAQUE COMPOSITIONS:

β-Fucosylamine B

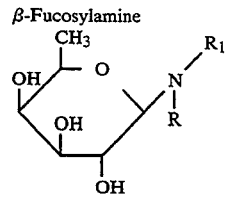

Lactosylamine C

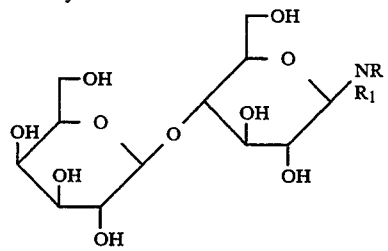

β-N-acetyl amino galactosylamine D

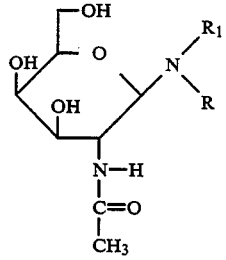

α-L-rhamnosylamine E

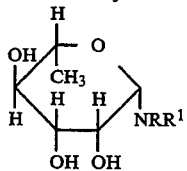

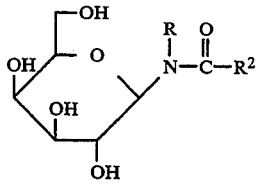 F

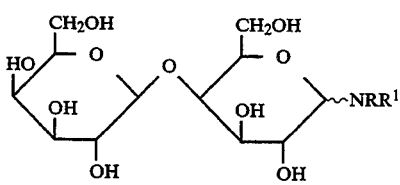 G

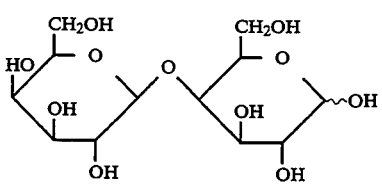 H

A compound of Structure F

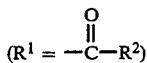

represents an amide derivative of the amino sugar and may be a preferred compound in certain oral hygiene formulations of the presented invention, due to the increased stability of the compound of structure F against hydrolysis. $R^2$ in Structure F is the same as R and $R^1$ described above.

Other examples of suitable amino sugars include but are not limited to:

N-piperidinyl β-D-galactopyranosylamine
N-2-bisphenyl β-D-galactopyranosylamine
N-benzyl β-D-galactopyranosylamine
N-cyclohexyl β-D-galactopyranosylamine
N-phenyl β-D-galactopyranosylamine
N-phenylazophenyl β-D-galactopyranosylamine
N-ethanoyl β-D-galactopyranosylamine
N-p-tolyl β-D-galactopyranosylamine
N-4-nitrophenyl β-D-galactopyranosylamine The preparation of the amino sugars is for the most part known. A reducing saccharide, which contains β-D-galactose, β-D-N-acetyl galactosamine, L-rhamnose or β-D-fucose, is mixed with the appropriate amine, $NHRR^1$ in water (preferably minimum amount of water is employed) and heated to at least about 80° C., typically for at least about 15–60 minutes. This procedure is applicable when R and/or $R^1$ on the amine contain at least 6 carbon atoms. The use of these amines is preferred in order to simplify synthesis. When an amine contains less than 6 carbon atoms or when ammonia is employed, it may be highly volatile, and the reaction may require lower temperatures and longer reaction times.

A compound of Structure F may be obtained from an amino sugar (which is prepared by a procedure described above) by a process described in U.S. Pat. Nos. 4,683,222 and 4,710,222, incorporated by reference herein. When $R^2$ is an amino acid compound F may be prepared by a process described by Garg et al. in "Synthetic N- and O-glycosyl Derivatives of l-asparagine, l-serine, and l-threonic," Advances in Carbohydrate Chemistry and Biochemistry, Vol. 43, 135–152 and by Marks et al. in J. Chem. Soc. 4872–4879 (1961), both articles incorporated by reference herein.

When both R and $R^1$ are hydrogen in the resulting amino sugar, it is preferred that $A^1$ contains more than one sugar moiety (e.g., $A^1$ is lactose or other disaccharide) in order to increase stability of the resulting amino sugar. When $A^1$ contains more than one sugar moiety, the stability may be further increased by reducing the amino sugar. The resulting reduced aminosugar must still contain a sugar moiety recognized by lectins on oral bacteria. An example of the amino sugar which was reduced after the parent saccharide, lactose, was aminated (according to the procedure described above) represented by structure I (N-alkyllactylamine):

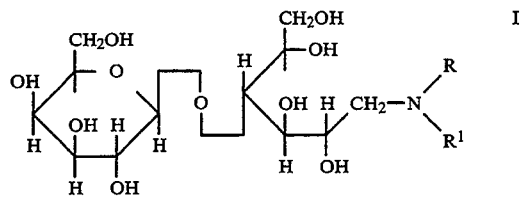

wherein R and $R^1$ are as described above, although when R and $R^1$ are hydrogens, compound G is particularly preferred.

The reduced amino sugar may be attained via a process described by P. Latge et al. in the J. Dispersion Science and Technology 12 (3 and 4), 227–237 (1991), incorporated by reference herein.

The amino sugars and their derivatives included in the present invention containing specific R and $R^1$ groups as described above and a specific sugar moiety recognized by lectins on oral bacteria (i.e. β-D-galactose, β-D-N-acetyl galactosamine, L-rhamnose or β-D-fucose) are capable of delivering various anti-plaque benefits. It has been found that these antiplaque agents are effective inhibitors of bacterial coaggregation and bacterial adhesion to solid surfaces and that they are also effective antimicrobial agents. In addition to their effects on specific bacterial adherence and their antimicrobial activity, amino sugars wherein R and/or R1 contain at least 8 carbon atoms, preferably from 8 to 24 carbon atoms, and most preferably from 8 to 16 carbon atoms were found to have potent dispersive effects on aqueous suspensions of *A. naeslundii* and *S.sanguis*. Therefore, these compounds represent surface-active antibacterial compounds which target in a stereospecific manner to bacterial binding proteins.

The amino sugars are employed in the present invention in an amount effective to inhibit plaque formation. The amount depends on the particular compound employed, but ranges generally from about 0.0001% to about 20%, preferably from about 0.001% to about 10%, and most preferably from about 0.01% to about 5%, by weight of the final composition.

The preferred oral compositions of the present invention are in the form of toothpaste, dental cream, gel or tooth powder, as well as mouthwash, pre-brushing rinse, or post-brushing rinse formulations, chewing gums and lozenges.

Ingredients typically included in toothpastes and gels may be used in toothpaste and gel compositions in accordance with the invention. Suitable ingredients include abrasive polishing materials, sudsing agents, flavoring agents, humectants, binders, sweetening agents, and water.

Mouthwashes are typically comprised of a water/alcohol solution, flavor, humectant, sweetener, foaming agent, and colorant.

Abrasives which may be used in the compositions of the invention include alumina and hydrates thereof, such as alpha alumina trihydrate, magnesium trisilicate, magnesium carbonate, aluminosilicates, such as calcined aluminum silicate and aluminum silicate, calcium carbonate, zirconium silicate, polymethyl methacrylate, powdered polyethylene, silica xerogels, hydrogels and aerogels and the like. Also suitable as abrasive agents are calcium pyrophosphate, insoluble sodium metaphosphate, calcium carbonate, dicalcium orthophosphate, particulate hydroxyapatite and the like. Depending on the form which the oral composition is to take, the abrasive may be present in an amount of from 0 to 70% by weight, preferably 1 to 70% by weight, more preferably from 10 to 70% by weight, particularly for toothpastes.

Humectants contemplated for use in the present invention include glycerol, polyol, sorbitol, polyethylene glycols, propylene glycol, hydrogenated partially hydrolyzed polysaccharides and the like. The humectants are generally present in amounts of from 0 to 80%, preferably 5 to 70% by weight, particularly for toothpastes. Thickeners suitable for use in the invention include silica. Thickeners may be present in toothpaste creams and gels at 0.1 to 20% by weight.

Binders suitable for use in the compositions of the invention include hydroxyethyl cellulose (Natrosol®), sodium carboxymethyl cellulose and hydroxypropyl cellulose (Klucel®), as well as xanthan gums, Irish moss and gum tragacanth. Binders may be present in the toothpaste of the invention to the extent of from 0.01 to 10%. Sweeteners suitable for use in the present dentifrice, preferably at levels of about 0.1% to 5%, include saccharin.

Suitable foaming agents include soap, anionic, cationic, nonionic, amphoteric and/or zwitterionic surfactants. These may be present at levels of 0 to 15%, preferably 0.1 to 15%, more preferably 0.25 to 10% by weight. It should be noted that many of the glycoside surface active agents described in the present invention also may be used as foaming agents at concentrations ranging from 0 to 15% by weight.

Certain pyrophosphate and other polyphosphate salts have been disclosed in U.S. Pat. Nos. 4,515,772 and 4,627,977 as being useful as anti-calculus agents. These include di- and tetra-alkali metal pyrophosphates wherein the alkali metals are preferably selected from the group consisting of sodium and potassium. Polyphosphate salts may be included generally in the amount such that it provides for at least 0.5% polyphosphate anions, the upper level being about 10%, preferably about 7.5%.

Various anionic polymers may be employed as anticalculus and/or antiplaque agents. Suitable polymers include carboxylate polymers, sulfonate polymers, polymers containing a sulfonate and a carboxylate moiety, carboxylate polymers containing phosphinate units, and mixtures thereof. The carboxylate polymers suitable in the present compositions are described by Gaffar et al., U.S. Pat. No. 4,808,400, incorporated by reference herein. Suitable carboxylate polymers containing mono- or disubstituted hypophosphite units along the polymer backbone are described in a U.S. Pat. No. 5,011,682 incorporated by reference herein. The anionic polymers may be included at a level from about 0.01 to about 10%, preferably from about 0.05 to about 5%.

Zinc salts are disclosed as anti-calculus and anti-plaque agents in U.S. Pat. No. 4,100,269 and in U.S. Pat. Nos. 4,416,867, 4,425,325 and 4,339,432. Preferred compositions of the invention include zinc salts, particularly zinc citrate. The zinc compounds may be present in the compositions in amounts sufficient to furnish about 0.01% to about 4% zinc, or preferably about 0.05% to about 1%, zinc ion.

Fluoride sources used in toothpastes such as sodium fluoride, stannous fluoride, sodium monofluorophosphate, zinc ammonium fluoride, tin ammonium fluoride, calcium fluoride and cobalt ammonium fluoride may be, and preferably are, included for delivering anti-caries benefit. Preferred compositions of the invention include the fluoride source. Fluoride ions are typically provided at a level of from 0 to 1500 ppm, preferably 50 to 1500 ppm, although higher levels up to about 3000 ppm may be used.

Flavors are usually included in toothpastes in low amounts, such as from 0.01 to about 5% by weight, especially from 0.1% to 5%.

Water-soluble antibacterial agents, such as chlorhexidine digluconate, hexetidine, alexidine, quaternary ammonium anti-bacterial compounds and water-soluble sources of certain metal ions such as zinc, copper, silver and stannous (e.g., zinc, copper and stannous chloride, and silver nitrate) may also be included.

Titanium dioxide is a suitable whitener.

Dyes/colorants suitable for dentifrices, i.e., FD&C Blue #1, FD&C Yellow #10, FD&C Red #40, etc., may be employed in the dentifrices of the invention.

Various other optional ingredients may be included in the compositions of the invention, such as preservatives, vitamins such as vitamin C and E, other anti-plaque agents such as stannous salts, copper salts, strontium salts and magnesium salts. Also included may be pH adjusting agents, anti-caries agents such as urea, calcium glycerophosphate, sodium trimetaphosphate, silicone polymers, plant extracts, desensitizing agents for sensitive teeth such as potassium nitrate and potassium citrate, and mixtures thereof.

Casein and/or its hydrolysate may be included as anticariess agents, e.g. at a level of 0.01 to 20% by weight, preferably 0.1 to 10%.

The corresponding compounds mentioned above which are used in toothpastes, are generally suitable within the ranges above for mouthwashes as well. The mouthwash can include ethanol at a level of from 0 to 60%, preferably from 5 to 30% by weight.

The inventive compositions may constitute an integral part of a toothpaste cream or gel, or mouthwash and applied during the regular brushing, or the compositions may be formulated and packaged as a separate treatment and applied separately before, after, and/or in between regular brushing times. The compositions may be applied by brushing, rinsing, chewing, etc.

The following specific examples further illustrate the present invention, but the invention is not limited thereto.

METHODS

Bacterial Coaggregation Assay

A bacterial coaggregation assay was used to determine the ability of various amino sugars to interfere with lectin-mediated binding among various bacterial species. For instance, many *Actinomyces naeslundii* strains coaggregate with *Streptococcus sanguis* as a result of binding between a lectin produced by the *A. naeslundii* cells and $\beta$-galactose-containing structures on the surface of the streptococci. For the present assay, *A. naeslundii* PK29 and *S. sanguis* G9B were cultured overnight in a medium containing 2.5% tryptone, 1.5% yeast extract, 0.1% magnesium sulfate, and 1.0% fructose. The cells were then washed twice in a 1.0 mM potassium phosphate buffer (pH=6.8) containing 1.0 mM calcium chloride, 0.1 mM magnesium chloride, and 50.0 mM potassium chloride (buffered KCl), after which they were resuspended in buffered KCl at an optical density (540 nm) of 1.5. The coaggregations were performed by combining 0.5 ml of each bacterial suspension with 0.2 ml of 5.0% bovine serum albumin (BSA) and 0.8 ml of an appropriate concentration of a targeted anti-plaque agent in 3.0 ml capped polystyrene cuvettes. The cuvettes (path length 1 cm) were gently inverted at room temperature, and the optical density (540 nm) was determined as a function of time (2.0 min intervals; 20 min).

The instrument employed to measure optical density was a variable wavelength spectrophotometer (Gilson Respons ® Spectrophotometer, bought from Gilson).

The activity of a tested compound was expressed as inhibition relative to buffer controls (i.e., % inhibition = [1 − change in optical density (inhibitor)]/change in optical density [control]) × 100.

Latex Bead-Bacterial Agglutination Assay

A latex bead agglutination assay was utilized to determine the effects of the amino sugars on lectin-mediated bacterial adherence to glycoprotein-coated surfaces. Latex beads (6.0 micrometer diameter) were prepared by suspending them in a 0.5 mg/ml solution of asialofetuin (a glycoprotein rich in oligosaccharide side chains which terminate in $\beta$-galactosyl groups) in 20.0 mM trishydroxyaminomethane buffer (ph=8.2) containing 0.73% glycine, 1.0% sodium chloride, 0.1 mM calcium chloride, and 0.02% sodium azide (TGS buffer). The beads were treated for 30.0 min at 37 degrees C. after which they were washed and resuspended in 0.1% BSA in TGS buffer. *A. naeslundii* PK29 cells were cultured as described in Bacterial Coaggregation Assay, washed, and resuspended in TGS buffer to an optical density (540 nm) of 1.5. The bacterial suspension (0.1 ml) and the prepared latex beads (1.0 ml) were combined with an appropriate concentration of inhibitor (0.8 ml) in 3.0 ml capped polystyrene cuvettes. The cuvettes were gently inverted at room temperature, and optical density (OD 540nm, 1 cm path length) was monitored at 2.0 min intervals for 20.0 min. The instrument employed was Gilson Response ®.

Antimicrobial Activity Determination

The antimicrobial activity of the targeted agents was assessed by determining the minimum inhibitory concentration (MIC). Pure cultures of various strains of oral bacterial species as indicated in Table 3 were combined with serial dilutions of the targeted agents in beef heart infusion broth (BHI); starting bacterial concentrations were approximately 1.0×10E6 colony forming units (CFU) per ml. The mixtures were incubated aerobically at 37 degrees C. and the optical density (540 nm, path length 1 cm) of the cultures was measured at 0.0, 24.0 and 48.0 hr using Bausch and Lomb Spec 20 variable wavelength spectrophotometer.

All amino sugars employed in the Examples had nitrogen conntected to anomeric carbon at the reducing end of the saccharide.

EXAMPLE 1

Preparation of Various Amino Sugars Suitable for Inclusion in the Inventive Compositions N-decyl galactosylamine $\beta$-D-galactose (10 g, 1 eq), decylamine (8.7 g, 1 eq), and water (2 g, 3eq) were heated in a reaction flask for 20 min at 80° C. Methanol/ethyl ether (50 v/50 v) was added, the product was filtered, washed with ethyl ether (2×50 ml) and dried, to give a 90% yield.

N-heptyl galactosylamine $\beta$-D-galactose (10 g, 1 eq), heptylamine (7.7 g, 1 eq) and water (2 g, 3 eq) were heated in a reaction flask at 80° C. for about 15 minutes. The sample was filtered and washed as described for the decyl derivative to give an 87% yield.

N-decyl lactosylamine $\alpha$-Lactose (10 g, 1eq), decylamine (9 g, 2 eq), and water (1.5 g, 2eq) were heated in a reaction flask for 30 min at 85° C. The reaction mixture was washed with acetone (2×100 ml) followed by hexane (2×50 ml). The product was dissolved in boiling MeOH (150 ml) and filtered to remove the unreacted lactose. The filtrate was cooled and ethyl ether (100 ml) was added. The product was isolated in about 35% yield.

N-heptyl lactosylamine $\alpha$-Lactose (10 g, 1 eq), heptylamine (3.83 g, 1 eq), and water (1 g) were heated in a reaction vessel at 85° C. for 30 min. MeOH (75 ml) was added and the mixture was filtered when. The product was filtered and dried to give a yield of 82%.

N-alkyl lactylamine (Structure I)

A solution of alkyl lactosylamine (0.01 mole) in water (70 ml) is cooled in an ice bath. A solution of NaBH$_4$ (0.013 mole) in water (15 ml) is then added dropwise. The mixture is warmed to 35–40° C. for 6 hours and then at ambient temperature for a further 15 hours. Amberlite IR-120 (H$^+$ form) is added under agitation until no more gas is evolved, and then a further 7 ml is added. The mixture is agitated for 30 minutes and treated with active carbon. After filtration on celite, the water is evaporated. The residue is taken up in methanol and evaporated five times in succession. A white, flaky powder is obtained on freeze drying.

EXAMPLE 2

Various amino sugars which are not suitable for inclusion in the inventive compositions were prepared in order to conduct comparative experiments.

N-alkyl glucosylamines

D-glucose was added to the molar equivalent of the appropriate alkyl amine in small amount of water and heated at 80° C. for 15 min. The product was washed with acetone, and then with ethyl ether and dried. Yields were in excess of 85%.

EXAMPLE 3

The ability of various amino sugars (prepared as described in Examples 1 and 2) to target to $\beta$-galactose-specific binding proteins on *A. naeslundii* and thus to interfere with coaggregation interactions between *A. naeslundii* and *S. sanguis* was investigated. Coaggregation of *Actinomyces naeslundii* PK29 and *Streptococcus sanguis* G9B was performed as described in the Methods section (Bacterial Coaggregation Assay) above. Inhibition was calculated as 1.0—the change in optical density (540 nm) in the sample containing compound tested/the change in optical density in the coaggregation buffer control. The inhibitory activity of the anti-plaque agents within the scope of the invention was compared to the inhibitory activity of parent saccharides and N-octyl glucosylmine (the latter compound does not contain $\beta$-galactose) which are not within the scope of the invention. The results that were obtained are summarized in Table 1.

TABLE 1

| Inhibitor | Concentration | % Inhibition |
|---|---|---|
| Galactose | 2.8 mMol/L | 10% |
| Lactose | 3.0 mMol/L | 61% |
| N-heptyl galactosylamine | 2.9 mMol/L | 20% |
| N-heptyl lactosylamine | 1.1 mMol/L | 23% |
| | 3.0 mMol/L | 63% |
| | 11.4 mMol/L | 79% |
| N-decyl lactosylamine | 1.0 mMol/L | 11% |
| | 2.1 mMol/L | 30% |
| | 3.0 mMol/L | 64% |
| N-octyl glucosylamine | 3.4 mMol/L | 0% |

As can be seen from Table 1, amino sugars within the scope of the invention (N-heptyl galactosylamine, N-heptyl lactosylamine, and N-decyl lactosylamine) were effective inhibitors of the β-galactose-specific coaggregation of A. naeslundii and S. sanguis. Compared to the parent saccharide, galactose, N-heptyl galactosylmine inhibited bacterial coaggregation approximately twice as much at the concentration tested; the N-heptyl and N-decyl lactosylmines showed slightly improved inhibition over their parent saccharide, lactose. That the inhibition by these compounds results from stereospecific interactions with β-galactose-specific binding proteins was indicated by the lack of inhibition by N-octylglucosylmine.

EXAMPLE 4

The ability of the amino sugars to inhibit bacterial adhesion was also tested using the latex bead assay described above (Methods section). This assay measures the ability of the test agents to interfere with bacterial adhesion to a glycoprotein-coated solid surface, which is analogous to pellicle coated tooth surface. Agglutination of asialofetuin-coated latex beads by A. naeslundii PK29 performed as described above. Inhibition was calculated as 1.0—the change in optical density (540 nm) in the sample containing the inhibitor/the change in optical density in the coaggregation buffer control. The results that were obtained are summarized in Table 2.

TABLE 2

| Inhibitor | Concentration | % Inhibition |
|---|---|---|
| Galactose | 2.8 mMol/L | 17% |
| N-decyl galactosylamine | 1.8 mMol/L | 51% |
| N-decyl glucosylamine | 1.8 mMol/L | 9% |

As shown in Table 2, N-decyl galactosylamine which is within the scope of the invention was a substantially more potent inhibitor of agglutination of glycoprotein-coated latex beads by A. naeslundii PK29 than galactose. The analogous compound made from glucose, N-decyl glucosylamine (not within the scope of the invention) was not an effective inhibitor of the agglutination.

EXAMPLE 5

The amino sugars within the scope of the invention and other compounds were tested for their bacteriostatic effects on the growth of several species of oral bacteria.

TABLE 3

| | Minimum Inhibitory Concentrations (% w/v) | | | | | | |
|---|---|---|---|---|---|---|---|
| Inhibitor Tested | Streptococcus sanguis | Streptococcus sobrinus | Actinomyces naeslundii | Porphyromonas gingivalis | Prevotella intermedius | Veillonella dispar | Neisseria subflava |
| Sodium dodecyl sulfate | 0.0015 | 0.006 | 0.0008 | 0.0002 | 0.0016 | 0.006 | 0.0008 |
| Heptyl galactosylmine | >0.1 | 0.1 | 0.025 | 0.0125 | — | — | 0.0125 |
| Heptyl lactosylmine | >0.1 | 0.1 | 0.05 | 0.05 | — | — | 0.05 |
| Decyl lactosylmine | 0.06 | 0.003 | 0.003 | — | — | — | 0.006 |
| Decyl glucosylmine | — | — | >0.5 | — | — | — | — |

As shown in Table 3, amino sugars within the scope of the invention (galactosylmine and lactosylmines) displayed substantial anti-microbial activity. Therefore, many of these molecules can deliver multiple anti-plaque benefits including anti-microbial activity, targeting to stereospecific bacterial binding proteins, and where applicable, surface-active properties.

By contrast, antimicrobial activity was not observed for amino sugars not within the scope of the invention (glucosylmine) which lacked a β-galactose moiety.

EXAMPLE 6

A typical toothpaste formula containing the amino sugar plaque inhibitor of the present invention is as follows:

| Toothpaste Formula (pH = 5-9) | |
|---|---|
| Component | Percent by Weight of the Final Composition |
| 70% Sorbitol | 64.0% |
| Abrasive Silica | 10.0% |
| Thickening Silica | 9.0% |
| Amino Sugar Antiplaque Agent | 5.0% |
| Polyethylene Glycol | 5.0% |
| Sodium Dodecyl Sulfate | 1.5% |
| Flavor | 1.0% |
| Sodium Saccharinate | 0.3% |
| Sodium Fluoride | 0.24% |
| Preservative (Benzoate) | 0.08% |
| Dye | <.01% |
| Sodium Carboxymethyl Cellulose | 0.15% |
| Water | to 100% |

EXAMPLE 7

A typical formula for a mouthwash containing the amino glycoside plaque inhibitor of the present invention is as follows:

| Mouthwash Formula (pH = 6.5) | |
|---|---|
| Component | Percent by Weight of Final Composition |
| Ethanol | 12.5% |
| 70% Sorbitol | 7.0% |
| Amino Glycoside Anti-plaque Agent | 5.0% |
| Tween 20 | 0.55% |
| Preservatives (parabens) | 0.2% |
| Flavor | 0.1% |

-continued

| Mouthwash Formula (pH = 6.5) | |
|---|---|
| Component | Percent by Weight of Final Composition |
| Dye | <.1% |
| Sodium Saccharinate | 0.65% |
| Sodium Chloride | 0.05% |
| Sodium Acetate | 0.015% |
| Acetic Acid | 0.015% |
| Water | to 100% |

Some suppliers for the materials employed in the invention have been mentioned in the description. Other materials in the description of the invention are available from the following suppliers:

| Material | Supplier |
|---|---|
| Bacteria: | |
| a) *Streptococcus sangius* G9B | In-house culture collection |
| b) *Actinomyces naeslundii* PK29 | Paul Kollenbrander, NIH, Bethes |
| c) *Neisseria subflava* A1078 | Phil Marsh, PHLS (centre for Appled Microbiology, Porton Down, UK |
| d) *Porphyromonas gingivalis* W83 | Phil Marsh, PHLS (centre for Appled Microbiology, Porton Down, UK |
| e) *Veillonella dispar* 17745 | In-house culture collection |
| f) *Streptococcus sobrinus* 6715 | In-house culture collection |
| g) *Prevotella intermedius* 25611 | In-house culture collection |
| 6.0 mM diameter styreme divinyl benzene Latex Beads | Sigma |
| Lactose | BBL - Becton Dickinson |
| Galactose | Fisher |
| Bovine Serum Albumin | Sigma |
| Asialofetuin | Sigma |
| Tween 20 ® (polysorbate 20) | ICI Americas Inc. |
| Plastic cuvettes - 4–5 ml polystyrene | Disposlab Kartell |
| Tryptone | Difco |
| Yeast Extract | BBL - Becton Dickinson |
| Beef Heart Infusion Broth | BBL - Becton Dickinson |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. An oral hygiene non-food composition comprising a suitable carrier and an effective antiplaque amount of at least one compound having a formula:

$$A^1\text{-NRR}^1$$

wherein
(i) $A^1$ is a saccharide comprising a sugar moiety recognized by lectins on oral bacteria selected from the group consisting of β-D-galactose, β-D-N-acetyl galactosamine, lactose, L-rhamnose and β-D-fucose;
(ii) nitrogen (N) is linked to the anomeric carbon at the reducing end of the saccharide $A^1$; and
(iii) R and $R^1$ are the same or different and are selected from the group consisting of hydrogen, an aliphatic hydrocarbon radical, an aromatic radical, and a cycloaliphatic radical.

2. The composition of claim 1 wherein R and $R^1$ are the same or different and contain a heteroatom, selected from the group consisting of nitrogen, oxygen, and sulphur.

3. The composition of claim 1 wherein R and $R^1$ are the same or different and both together contain from 1 to 36 carbon atoms.

4. The composition of claim 3 wherein R and $R^1$ are the same or different and both together contain from 6 to 36 carbon atoms.

5. The composition of claim 1 wherein $A^1$ is β-D-galactose.

6. The composition of claim 1 wherein $A^1$ is lactose.

7. The composition of claim 1 wherein $A^1$ is β-D-galactose, $R^1$ is hydrogen and R is a straight chain hydrocarbon radical having from 6 to 18 carbon atoms.

8. The composition of claim 1, wherein $$R^1 = -\overset{\overset{\displaystyle O}{\|}}{C} - R^2$$

wherein $R^2$ is selected from the group consisting of hydrogen, an aliphatic radical, and a cycloaliphatic radical and may contain a heteroatom selected from the group consisting of nitrogen, oxygen, and sulphur.

9. The compositions of claim 8 wherein $R^2$ is an amino acid.

10. The composition of claim 1 wherein $A^1$ is a reduced saccharide comprising a sugar moiety recognized by lectins on oral bacteria selected from the group consisting of β-D-galactose, β-D-N-acetyl galactosamine, lactose, L-rhamnose and β-D-fucose.

11. The composition of claim 10 wherein the antiplaque active is N-alkyl lactylamine.

12. The composition of claim 1 wherein the composition further comprises a source of zinc ion.

13. The composition of claim 1 wherein the composition further comprises a source of fluoride ion.

14. The composition of claim 1 wherein the amount of the compound is in the range of from 0.0001% to 20%.

15. The composition of claim 1 wherein the molecular weight of the compound is not greater than 30,000 Daltons.

16. The composition of claim 15 wherein the molecular weight of the compound is from 200 to 2,000 Daltons.

17. A method of inhibiting bacterial aggregation in an oral cavity comprising applying into said oral cavity a non-food composition comprising a suitable carrier and an effective plaque-inhibiting amount of at least one compound having a formula:

$$A^1\text{-NRR}^1$$

wherein
(i) $A^1$ is a saccharide comprising a sugar moiety recognized by lectins on oral bacteria selected from the group consisting of β-D-galactose, β-D-N-acetyl galactosamine, L-rhamnose and β-D-fucose;
(ii) nitrogen (N) is linked to the anomeric carbon at the reducing end of the saccharide $A^1$; and
(iii) R and $R^1$ are the same or different and are selected from the group consisting of hydrogen, an aliphatic hydrocarbon radical, an aromatic radical, and a cycloaliphatic radical.

* * * * *